United States Patent [19]

Epperly et al.

[11] Patent Number: 5,034,020

[45] Date of Patent: Jul. 23, 1991

[54] METHOD FOR CATALYZING FUEL FOR POWERING INTERNAL COMBUSTION ENGINES

[75] Inventors: W. Robert Epperly, New Canaan; Barry N. Sprague, Bethlehem, both of Conn.

[73] Assignee: Platinum Plus, Inc., Rowayton, Conn.

[21] Appl. No.: 380,891

[22] Filed: Jul. 17, 1989

Related U.S. Application Data

[63] Continuation-in-part of Ser. No. 291,245, Dec. 28, 1988, which is a continuation-in-part of Ser. No. 897,864, Aug. 19, 1986, Pat. No. 4,892,562, and Ser. No. 897,869, Aug. 19, 1986, Pat. No. 4,891,050.

[51] Int. Cl.$^5$ .................................................. C10L 5/00
[52] U.S. Cl. ..................................... 44/358; 350/414; 350/439; 350/447; 350/451
[58] Field of Search .................... 44/52, 56, 57, 67, 63, 44/70, 72, 77, 68, 358, 360, 361, 362; 556/32, 136, 137

[56] References Cited

U.S. PATENT DOCUMENTS

| 2,875,223 | 2/1959 | Pedersen et al. | 534/12 |
|---|---|---|---|
| 3,159,659 | 12/1964 | Pruett et al. | 556/136 |
| 3,328,440 | 6/1967 | Shapiro et al. | 556/136 |
| 4,207,078 | 6/1980 | Sweeney et al. | 44/68 |
| 4,242,099 | 12/1980 | Malec | 44/53 |
| 4,295,816 | 10/1981 | Robinson | 431/4 |
| 4,469,638 | 9/1984 | Bonnemann | 556/136 |
| 4,603,275 | 7/1986 | Chandra et al. | 556/136 |

FOREIGN PATENT DOCUMENTS

WO86/03492 6/1986 European Pat. Off. ................ 44/67

OTHER PUBLICATIONS

Maitlis, The Organic Chemistry of Palladium, Academic Press, N.Y., pp. 68,70,76,77,83,92,102,103,136,158,165,202–204,228,242,-249,257–258 (1971).
German Patent No. 2,500,683 Abstract 76-56183X, Brantl.
Belluco, Organometallic and Coordination Chemistry of Platinum, Academic Press, N.Y., pp. 221,222,226,232,295–297, 441–442,449,454 and 455 (1974).
Deganello, Transition Metal Complexes of Cyclic Polyolefins, Academic Press, N.Y., pp. 97–100, 102, 277–278, 281–283, 288–291 (1979).
Dickson, Organometallic Chemistry of Rhodium and Iridium, Academic Press, N.Y., pp. 167–169, 178–180, 198–200, 220–226, 248,258–260, 264, 271 and 277 (1983).
Wilkinson et al., "Comprehensive Organometallic Chemistry", vol. 6, Pergamon Press, 1982.
Chemical Abstracts 76 1125465p (1792).
Chemical Abstracts 76 11355g (1792).
Chemical Abstracts 82 4403z (1975).
Chemical Abstracts 97 110175w (1982).
Chemical Abstracts 97 110181v (1982).

*Primary Examiner*—Margaret B. Medley
*Attorney, Agent, or Firm*—St. Onge Steward Johnston & Reems

[57] ABSTRACT

The invention presented is a method for catalyzing fuel for powering internal combustion engines. The method comprises admixing with fuel an additive composition comprising at least one fuel-soluble platinum group metal compound in an amount effective to supply from 0.01 to 1.0 parts per million of platinum group metal per part of fuel.

12 Claims, No Drawings

METHOD FOR CATALYZING FUEL FOR POWERING INTERNAL COMBUSTION ENGINES

RELATED APPLICATIONS

This application is a continuation-in-part of copending and commonly assigned U.S. patent application entitled "Method for Reducing Emissions From or Increasing the Utilizable Energy of Fuel For Powering Internal Combustion Engines," Ser. No. 07/291,245, filed in the names of Epperly, Sprague, Kelso and Bowers on Dec. 28, 1988, which in turn is a continuation-in-part of copending and commonly assigned U.S. patent application entitled "Diesel Fuel Additives and Diesel Fuels Containing Soluble Platinum Group Metal Compounds and Use in Diesel Engines", Ser. No. 06/897,864, filed in the names of Bowers and Sprague on Aug. 19, 1986, now U.S. Pat. No. 4,892,562, and copending and commonly assigned U.S. patent application entitled "Gasoline Additives and Gasoline Containing Soluble Platinum Group Metal Compounds and Use in Internal Combustion Engines", Ser. No. 06/897,869, filed in the names of Bowers and Sprague on Aug. 19, 1986, now U.S. Pat. No. 4,891,050. The disclosures of each of these prior applications is hereby incorporated by reference herein.

TECHNICAL FIELD

The present invention relates to improving the performance of internal combustion engines utilizing hydrocarbon fuels including gasoline, gasohol and diesel fuel, and, more particularly, to the use of additives and fuels which burn more efficiently and with reduced noxious emissions.

BACKGROUND ART

Prior investigations involving the use of platinum group metals in internal combustion engines have led to the development of the catalytic converter for emissions reduction. Efforts are under way to also achieve such results through better combustion conditions through engine design and fuel additives. Mechanical equipment has become one acceptable alternative to accomplish desired combustion improvements. These efforts in engine design have provided significant improvements, but the objectives of improved operating efficiency and reduced noxious emissions are difficult to achieve simultaneously.

Experiences to date with fuel additives have been less successful. For example, Lyons and McKone disclose in U.S. Pat. Nos. 2,086,775 and 2,151,432 adding from 0.001-0.085% (i.e. from 10 to 850 parts per million) of an organometallic compound or mixture to a base fuel such as gasoline, benzene, fuel oil, kerosene or blends to improve various aspects of engine performance. Included among the metals disclosed in these patents are the platinum group metals platinum and palladium. In both patents the preferred organometallic compounds are the beta diketone derivatives and their homologues such as the metal acetylacetonates, propionylacetonates, formylacetonates, and the like. The two Lyons and McKone patents state that concentrations of from 0.001-0.04%, (i.e. from 10 to 400 parts per million) are not effective to improve combustion efficiency as introduced, but may become so under prolonged use as catalytically active deposits are built up in the combustion chamber. The disclosures further state that about 0.01% (i.e. 100 ppm) of the organometallic compound is usually sufficient, once the requisite amount of catalytically active deposits has been built up, to perpetuate that amount of deposits by replacement of losses therefrom. The compounds disclosed were therefore not capable of generating any instantaneous catalytic effect at low concentrations, and in higher concentrations would provide no economic benefit. This fact is confirmed in U.S. Pat. No. 2,460,780 to Lyons and Dempsey at col. 1, lines 11-36.

The Lyons and Dempsey patent relates principally to employing catalysts which are soluble in water or other "internal liquid coolants" such as alcohol or soluble glycols or aqueous solutions of these. While catalyst levels based on the weight of metal compounds as low as 0.001% are disclosed, it is stated that for immediate catalytic effect, the catalyst compounds may be present at a level of at least 1% of the weight of the operating fuel charge. No disclosure is given of fuel soluble catalysts at levels below 0.01% or without oxygenated solvents. Moreover, where alcohol and glycols are employed with water soluble catalysts, they are disclosed principally as solublizing carriers for catalysts and for their known internal cooling function at high load.

Robinson, in U.S. Pat. No. 4,295,816, discloses an elaborate delivery system for introducing water soluble platinum group metal salts through the air intake of internal combustion engines to deliver platinum group metal catalysts to the combustion chamber at a level no greater than 9 milligrams of catalyst per kilogram of fuel. The equipment disclosed by Robinson, unfortunately, is far more complicated than would be desired for automotive operators and the water soluble salts employed, e.g. halides, have disadvantages alone or when dissolved.

In German Offenlegungsschrift 2,500,683, Brantl discloses a wide variety of catalytic metals which may be added to hydrocarbon fuels to reduce nitrogen monoxide and oxidize carbon monoxide at the moment of combustion in internal combustion engines. Among the metals disclosed are metal complexes of the metals ruthenium, rhodium, palladium, osmium, iridium and platinum, with different ligands, which can be added to the fuel individually or as a mixture. For these platinum group metals, broad concentration ranges of from 0.347 to 3.123 grams per liter of fuel are suggested for the various compositions listed in the disclosure, with the range for particularly favorable results being from 0.868 to 1.735 grams per liter of fuel. Considering the cost of these metals and the compositions containing them, there is a negative incentive for employing them at the high levels stated by the disclosure as effective. Moreover, the disclosed tetramethyl platinum compound is not known to exist.

Although the prior art has identified the platinum group metal compounds as superior catalysts for improving fuel efficiency and reducing noxious emissions, an ongoing problem has been to produce a platinum group metal compound which is sufficiently stable for packaging and delivery to the engine as well as having sufficient solubility in the fuel and insolubility in water which may be contained with the fuel. Unfortunately, nothing in the prior art has provided such compounds.

DISCLOSURE OF INVENTION

The present invention comprises a method for catalyzing fuels for internal combustion engines in order to reduce emissions from and/or increase the utilizable energy of the fuels. The method involves the application of certain platinum group metal compounds which are directly soluble in the fuels. The compounds, preferably in combination with a solvent for them which is also miscible in the fuel, are most advantageously employed at very small but catalytically effective levels to provide from about 0.01 to about 1.0 parts of platinum group metal per 1 million parts of fuel (ppm). For the purposes of this description, all parts per million figures are on a weight to volume basis, i.e., grams/million cubic centimeters (which can also be expressed as milligrams/liter), and percentages are given by weight, unless otherwise indicated.

Suitable platinum group metal compounds for use in this invention include the following:

a) palladium acetylene complexes having the general formula

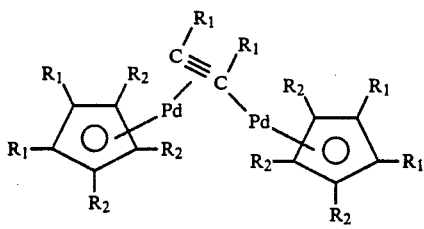

wherein $R^1$ is aryl or alkyl and $R^2$ is aryl;

b) metal allyl complexes having the general formula

wherein $M^1$ is rhodium or iridium;

c) platinum (IV) compositions having the general formula

wherein $R^3$ is aryl or alkyl or mixtures thereof; and $R^4$ is hydroxyl, acetylacetonate, cyclopentadiene or pentamethyl cyclopentadiene; and d) a composition of the general formula

wherein $L^1$ is substituted or unsubstituted butadiene or cyclohexadiene; $M^2$ is rhodium or iridium; and $R^5$ is cyclopentadiene or pentamethyl cyclopentadiene.

DETAILED DESCRIPTION OF THE PREFERRED EMBODIMENT

The fuels used in internal combustion engines for which the method of this invention is effective include hydrocarbon fuels such as gasoline, diesel fuel and gasohol. Other fuels such as methane, propane, butane, residual fuel, kerosene and jet fuel can also be included consistent with engine design, availability and economics. For the purposes of this description, the term "gasoline" can be defined as a mixture of volatile hydrocarbons, including paraffinic, naphthenic, aromatic and olefinic hydrocarbons, having a boiling range from about 75° F. to 450° F., for use in a spark-ignited internal combustion engine and having an octane rating [(research+motor)/2] of at least 80, typically about 87 to 89 or above, and according to the most preferred aspects of the invention, having less than about 1.4 grams per gallon of lead. Most preferably, the gasoline will be "unleaded" and contain no more than about 0.05 grams of lead per gallon and no more than about 0.1% of sulfur. Gasoline typically has a heating value of about 19,700 British Thermal Units (BTU) per pound. Moreover, the term "diesel fuel" can be defined as fuel oil Nos. 2 or 4, petroleum distillates or No. 6 residual fuel of volatility and cetane number characteristics effective for the purpose of fueling a wide range of internal combustion diesel engines; and the term "gasohol" can be defined as a blended mixture of gasoline, as defined above, and an alcohol, such as methanol, ethanol, tertiary butyl alcohol, isopropanol and/or pentanol, optionally with water and/or surfactants, of volatility and octane number characteristics effective for the purpose of fueling internal combustion gasoline engines.

The method of the present invention comprises admixing with the fuel an additive which comprises a fuel-soluble, nonionic, organometallic platinum group metal coordination composition. The composition should be temperature stable, should not contain a substantial amount of phosphorus, arsenic, antimony or halides and should have a partition ratio sufficient to maintain significant preferential solubility in the fuel. The nonionic, organic nature of the composition provides solubility in the fuels discussed above, thereby facilitating the introduction of the additive into the combustion chamber. Without such solubility, much of the additive would precipitate in the fuel tank or fuel lines of the engine prior to introduction into the combustion chamber.

The invention identifies temperature stability of the additive as important in practical and operational terms. In a commercial setting, a fuel additive is packaged and then can often sit on a store shelf or in a delivery truck for extended periods of time during which the additive can be exposed to great variations in temperature. If the breakdown temperature of the additive is not sufficiently high (i.e. if the additive is not temperature stable at the temperatures to which it is expected to be exposed), then the packaged additive will quickly break down and become virtually useless. Moreover, breakdown of the additive after mixing with the fuel will render the additive insoluble in the fuel, since the solubility is provided by the organic functional groups. Such loss of solubility will cause the additive to precipitate and not reach the combustion chamber, as discussed above. Typically, the breakdown temperature of the additive should be at least about 40° C., preferably at least about 50° C. in order to protect against most temperatures to which it can be expected to be exposed. In some circumstances, it will be necessary that the breakdown temperature be no lower than about 75° C.

In general, the additive comprises the platinum metal group composition as well as an oxygenated solvent therefor, as will be discussed in more detail below. The nonionic, organic nature of the platinum group metal composition helps to maintain the composition in solution in the solvent, thereby preventing "plating out" of the platinum group metal composition in the packaging medium.

As noted, the additive of the present invention should not contain a substantial amount of objectionable functional groups such as phosphorus, arsenic, antimony and, especially, halides, which have significant disadvantages like "poisoning" or otherwise reducing the effectiveness of the platinum group metal composition catalyst. Halides have the additional undesirable effect of rendering a platinum group metal more volatile, leading to reduction of the amount of platinum group metal in the combustion chamber and engine system. A substantial amount of such functional groups is considered an amount effective to significantly reduce the effectiveness of the catalyst. Preferably, the purified platinum group metal additive composition contains no more than about 500 ppm (on a weight per weight basis) of phosphorus, arsenic, antimony or halides, more preferably no more than about 250 ppm. Most preferably, the additive contains no phosphorus, arsenic, antimony or halides. Such objectionable functional groups can be minimized in several ways. The platinum group metal composition can be prepared in a process which utilizes precursors or reactant compositions having a minimum of such functional groups; or the additive can be purified after preparation. Many acceptable methods of purification are known to the skilled artisan.

One preferred method of purifying the platinum group metal additive to remove halides is a process utilizing silver salts having non-halide anions which are harmless as compared to the halides being replaced and involves reacting them with the platinum group metal compound, whereby the halides in the composition are replaced by the anion of the silver salt (which can be any silver salts of carboxylic acids, such as silver benzoate; or silver nitrate) and the resulting composition is free of halides, plus a silver halide is produced. For instance, a slurry or solution in a polar solvent, such as acetone or an alcohol, and water of silver nitrate or silver benzoate can be prepared and reacted with the platinum group metal composition. The resultant platinum group metal composition is a benzoate or nitrate salt with silver halide also being produced. This process can be expected to reduce the halide content of a sample by at least about 50%, and even as high as about 90% and higher.

The relative solubility of the additive in the fuel and water is also important since there is often a substantial amount of water admixed in with fuel. This relative solubility can be referred to as the partition ratio and is expressed as the ratio of the amount in milligrams per liter of composition which is present in the fuel to the amount of which is present in the water. The partition ratio can be most easily measured by use of a 100 milliliter (ml) sample which is 90% fuel and 10% water. The preferential solubility of the additive in fuel as compared to water (expressed as the partition ratio) can be critical because if a substantial amount of the additive is dissolved in the water which may be present, the overall effectiveness of the additive is proportionally reduced.

When the fuel being utilized is gasoline or diesel fuel, this partition ratio should be at least about 25 and most preferably greater than about 50. Because of the increased solubility of an organic platinum group metal composition in water as compared to gasohol, the partition ratio in gasohol could often not be expected to be as high but, rather, it could be as low as 10, and even 2. Such a low partition ratio is not desired (although as low as 5 in gasohol could be considered marginally operable). Indeed, partition ratios of much higher, i.e., at levels of those for gasoline or diesel fuel, are sought. In order to reduce the water susceptibility of the platinum group metal composition, it is desired that the composition have at least one platinum group metal-to-carbon covalent bond. A platinum group metal-to-oxygen or platinum group metal-to-nitrogen bond is acceptable when the ligand is neutral (as will be discussed in more detail below), but there must also be at least one metal to carbon bond.

Platinum group metals include platinum, palladium, rhodium, ruthenium, osmium and iridium. Compounds including platinum, palladium and rhodium, especially platinum alone or possibly in combination with rhodium are preferred in the practice of this invention since the vapor pressure of these metals is sufficiently high to form engine deposits which have the desired effect on combustion.

Specific suitable compounds according the present invention include those platinum metal group-containing compositions selected from the group consisting of a) palladium acetylene complexes having the general formula

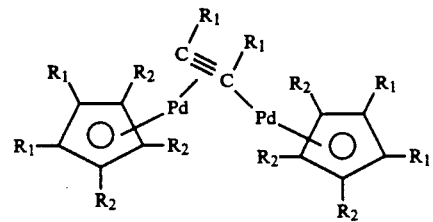

wherein $R^1$ is aryl or alkyl; and $R^2$ is aryl;

b) metal allyl complexes having the general formula

$M^1(C_3H_5)_3$ wherein $M^1$ is rhodium or iridium;

c) platinum (IV) compositions having the general formula

$R_3{}^3PtR^4$ wherein $R^3$ is aryl, alkyl or mixtures thereof; and $R^4$ is hydroxyl (—OH), acetylacetonate (—CH$_3$(COCH$_3$)$_2$), cyclopentadiene or pentamethyl cyclopentadiene (exemplary of which is trimethyl platinum hydroxide); and d) a composition of the general formula

$L^1M^2R^5$ wherein $L^1$ is substituted or unsubstituted butadiene or cyclohexadiene; $M^2$ is rhodium or iridium; and $R^5$ is cyclopentadiene or pentamethyl cyclopentadiene (exemplary of which are butadiene rhodium cyclopentadiene and butadiene iridium cyclopentadiene.

For the purposes of this description, the term "aryl" can be taken to mean any substituted or unsubstituted organic radical derived from an aromatic hydrocarbon by the removal of one atom, such as phenyl or pentamethyl phenyl, etc.; the term "alkyl" can be taken to mean any substituted or unsubstituted monovalent radical derived from an aliphatic hydrocarbon by removal of one hydrogen, such as methyl, ethyl, etc.; the term "lower alkyl" can be taken to mean an alkyl having 6 or fewer carbon atoms; the term "acetylene" can be taken to mean an unsatured alkyl having at least one carbon-to-carbon triple bond; and the term "allyl" can be taken to mean a resonance structure wherein two or three carbon atoms of the allyl group ($C_3H_5$) are bound to the metal atom. When a group or compound is indicated as "substituted," it is meant that the group contains at least one substituent which is a cyclic, straight or branched chain hydrocarbon, including nitrogenated and oxygenated hydrocarbons (i.e., hydrocarbons containing nitrogen or oxygen, respectively), which can be substituted themselves. "Unsubstituted" is meant to indicate that the group or compound contains no such substituents.

The synthesis of the preferred compounds is relatively straightforward, with the most care being taken to avoid "contamination" of the product by the objectionable functional groups discussed above. For instance, the most preferred synthetic route for production of the noted acetylene compounds is by reacting the trimeric palladium salt of a carboxylic acid ($[Pd(OOCR^6)_2]_3$), where $R^6$ is alkyl such as methyl or ethyl, or aryl such as phenyl, such as palladium acetate, propionate or benzoate, with a substituted acetylene, such as diphenylacetylene or methylphenylacetylene, in the presence of a polar solvent, such as an alcohol like methanol ($CH_3OH$). For example, when the reactants are palladium acetate and diphenylacetylene, the product is $\mu$-diphenylacetylene bis($\eta^5$ pentaphenyl cyclopentadiene) dipalladium, which has the general formula

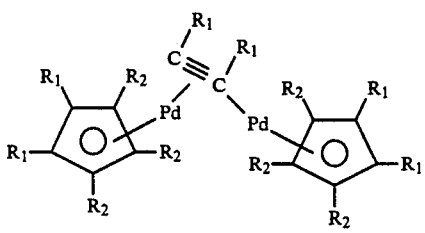

where $R^1$ and $R^2$ are each phenyl.

The disclosed metal allyl compositions can be prepared by reacting commercially available rhodium or iridium halides, such as $RhCl_3$ or $IrCl_3$, with an allyl Grignard reagent, such as $C_3H_5MgBr$, in a 3:1 molar ratio to produce the desired metal allyl and MgBrCl.

The platinum (IV) compositions can be prepared, for instance, by reacting $R_3^7PtX$, where $R^7$ is aryl or alkyl, such as phenyl, benzyl or methyl or mixtures and X is a halide, with $NaR^8$, where $R^8$ is cyclopentadiene or pentamethyl cyclopentadiene.

Reaction of the $R_3^7PtX$ complex with aqueous acetone solutions containing a silver compound such as $Ag_2O$ results in a product where $R^4$ is hydroxyl. Alternatively, treatment of the $R_3^8PtX$ complex with a solution of acetylacetone in alcoholic potassium hydroxide results in a product where $R^4$ is acetyl acetonate.

The compounds of the formula $L^1M^2R^5$ can be prepared by reacting commercially available metal halides with butadiene and cyclohexadienes and then reacting with a Grignard reagent having the formula $R_5MgX$, where X is a halide.

Advantageously, in the Grignard-type syntheses, the Grignard reagent can be replaced by one having the formula RZ where Z is commonly Na, Li, K or Tl. This is especially preferred since the halides which are present in a Grignard reagent are eliminated, providing less halides in the final product and also advantageously producing a higher yield of the desired product.

The additive compositions according to the invention improve operating efficiency of internal combustion engines in terms of increased power output per unit of fuel burned, which results in improved fuel economy and/or greater horsepower per revolutions per minute (rpm) and reduced emissions of particulates and noxious gases such as carbon monoxide, hydrocarbons and nitrogen monoxide. Additionally, the additive compositions of this invention can function to improve the performance of a diesel particulate trap by providing or replenishing catalyst metals on the trap, which function to facilitate the "burning off" of trapped particulates, thusly increasing the amount of time between regenerations, and increasing the effectiveness and the life of the trap, and decreasing the fuel penalty associated with use of a diesel trap. A portion of the catalyst metals are vaporized in the combustion chamber and travel in the exhaust gases to the trap where they perform this function.

The inventive compositions can also be used beneficially with a catalytic converter. Vaporized catalyst metal compositions can travel from the combustion chamber and replenish the converter, thus extending the effectiveness and life of the converter. In fact, a converter having no catalyst present can be installed and, over time, the practice of this invention will function to actually "load" the converter with catalyst.

The additives when added to diesel fuel and supplied to an engine are believed to reduce the so-called "delay period" which occurs immediately after injection of the fuel into the combustion chamber is initiated, due to improvement in the shape of the indicator diagram. This reduction of delay between vaporization and ignition can explain the improvements noted by the present invention but not suggested by the prior art; however, this theoretical explanation is presented only because it is the best available and there may well be others which even better explain the surprising results noted. The additives provide beneficial results over long periods of continuous use in internal combustion diesel engines.

Timing of fuel injection during the compression stroke is an important consideration in a diesel engine. Timing is optimized to maximize fuel economy while meeting important emissions standards. As already pointed out, the inventive fuel additive reduces the delay time until fuel starts to burn and its effect is similar to advancing the time of fuel injection before top dead center. As a result, there is an opportunity to re-optimize fuel injection timing (i.e., delaying injection) when the additive is used in order to optimize the overall system (improve fuel economy while meeting emission standards).

The additives are believed to improve combustion efficiency in gasoline- or gasohol-powered internal combustion engines by speeding up flame initiation from the spark and increasing subsequent flame speed. It is well known that each cycle in the spark ignition engine varies around the mean optimum pressure pattern with maximum pressure shortly after top dead center. The method of this invention is believed to reduce the so called "cyclic variation" from this optimum and thus increases the power for the same amount of fuel, which improves fuel consumption. This theory is provided to help explain the unexpected results achieved in gasoline- or gasohol-powered internal combustion engines, but it is not meant to be limiting in any regard. The additives also provide beneficial results over long periods of continuous use in internal combustion gasoline or gasohol engines.

The additive will be added to the fuel in an amount effective to improve engine performance, in terms of operating efficiency or emissions reduction. Typically, the platinum group metal compound will supply an amount of the platinum group metal within a range of about 0.01 to 1.0 parts of the platinum group metal per one million parts of fuel (ppm w/v). A more preferred range is from about 0.05 to 0.5 ppm and, most preferably, the platinum group metal will be supplied at a level of from about 0.10 to 0.30 ppm on the same basis.

The additive composition will preferably include a solvent which is soluble in the fuel, preferably made of a mixture of a carrier such as kerosene, xylene or other hydrocarbons plus certain solvents which provide enhancements in the effectiveness of the platinum group metal compound. Among the preferred solvents are oxygenated hydrocarbons, such as alcohols, heterocyclic oxygen compounds and ethers. Particularly preferred compounds are: 1 to 4 carbon alcohols, especially ethanol; acetone; tetrahydrofuran; and methyl tertiary butyl ether. Octyl nitrate also functions well in diesel fuel additives.

The fuel additive compositions may also contain other additives, such as detergents, antioxidants and octane improvers which are known as beneficial to engine performance, but the use of such is not an essential feature of the invention.

The total amount of solvent and other additives used will depend on the dosage of platinum group metal composition required and on what is a convenient concentration to handle relative to the amount of fuel to be treated. Typically, solvent (plus other like additive) volumes of about 0.1 to about 40.0 liters/gram of platinum are acceptable.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

We claim:

1. A method for catalyzing fuel for powering internal combustion engines, comprising admixing with said fuel an additive composition comprising at least one fuel-soluble platinum group metal compound selected from the group consisting of:
   a) palladium acetylene complexes having the general formula

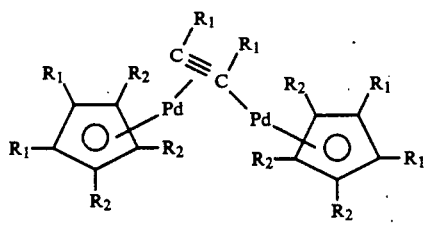

wherein $R^1$ is aryl or alkyl; and $R^2$ is aryl;
   b) metal allyl complexes having the general formula

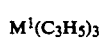

wherein $M^1$ is rhodium or iridium;
   c) platinum (IV) compositions having the general formula

wherein $R^3$ is aryl, alkyl or mixtures thereof; and $R^4$ is hydroxyl, acetylacetonate, cyclopentadiene or pentamethyl cyclopentadiene; and
   d) a composition of the general formula

wherein $L^1$ is substituted or unsubstituted butadiene or cyclohexadiene; $M^2$ is rhodium or iridium; and $R^5$ is cyclopentadiene or pentamethyl cyclopentadiene, wherein said platinum group metal compound is provided in an amount effective to supply from 0.01 to 1.0 parts per million of platinum group metal per part of fuel.

2. The method of claim 1 wherein $R^1$ and $R^3$ are phenyl or lower alkyl, $R^2$ is phenyl and $R^4$ is cyclopentadiene.

3. The method of claim 1 wherein said additive further comprises a fuel-soluble solvent for said composition in an amount of about 0.1 to about 40.0 liters per gram of platinum group metal.

4. The method of claim 1 wherein said additive comprises $Rh(C_3H_5)_3$ or $Ir(C_3H_5)_3$ and the metal is present in an amount of from 0.01 to 0.5 parts per million of the fuel.

5. The method of claim 3 wherein said additive comprises trimethyl platinum hydroxide and the platinum is present in an amount of from 0.01 to 0.5 parts per million of the fuel.

6. The method of claim 3 wherein said additive comprises butadiene rhodium cyclopentadiene or butadiene iridium cyclopentadiene and the metal is present in an amount of from 0.01 to 0.5 parts per million of the fuel.

7. The method of claim 3 wherein the fuel is diesel fuel and said solvent is octyl nitrate.

8. The method of claim 3 wherein the fuel is gasoline and said solvent is ethanol, acetone, tetrahydrofuran, methyl tertiary butyl ether or mixtures thereof.

9. A method for improving the operation of a diesel engine particulate trap comprising admixing with the diesel fuel used to power the diesel engine an additive which comprises a fuel-soluble, nonionic, organometallic platinum group metal coordination composition wherein said composition is selected form the group consisting of:
   a) palladium acetylene complexes having the general formula

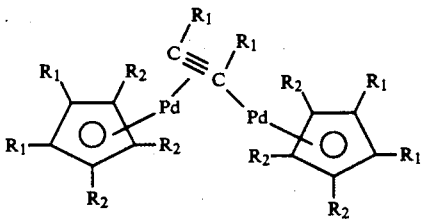

wherein $R^1$ is aryl or alkyl; and $R^2$ is aryl;
   b) metal allyl complexes having the general formula

wherein $M^1$ is rhodium or iridium;
   c) platinum (IV) compositions having the general formula

wherein $R^3$ is aryl, alkyl or mixtures thereof; and $R^4$ is hydroxyl, acetylacetonate, cyclopentadiene or pentamethyl cyclopentadiene; and d) a composition of the general formula $$L^1M^2R^5$$

wherein $L^1$ is substituted or unsubstituted butadiene or cyclohexadiene; $M^2$ is rhodium or iridium; and $R^5$ is cyclopetadiene or pentamnethyl cyclopentadiene, wherein said platinum group metal compound is provided in an amount effective to supply from 0.01 to 10.0 parts per million of platinum group metal per part of fuel and further wherein said platinum group metal compound is vaporized in the combustion chamber and travels to and replenishes the diesel trap.

10. The method of claim 9 wherein $R^1$ and $R^3$ are phenyl or lower alkyl, $R^2$ is phenyl and $R^4$ is cyclopentadiene.

11. A method for improving the operation of a catalytic converter comprising admixing with the fuel used to power an engine an additive which comprises a fuel-soluble, nonionic, organometallic platinum group metal coordination composition wherein said composition is selected form the group consisting of a) palladium acetylene complexes having the general formula

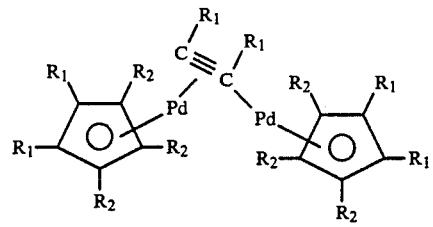

wherein $R^1$ is aryl or alkyl; and $R^2$ is aryl;

b) metal allyl complexes having the general formula $$M^1(C_3H_5)_3$$

wherein $M^1$ is rhodium or iridium;

c) platinum (IV) compositions having the general formula $$R_3^3PtR^4$$

wherein $R^3$ is aryl, alkyl or mixtures thereof; and $R^4$ is hydroxyl, acetylacetonate, coclopentadiene or pentamethyl cyclopentadiene; and d) a composition of the general formula $$L^1M^2R^5$$

wherein $L^1$ is substituted or unsubstituted butadiene or cyclohexadiene; $M^2$ is rhodium or iridium; and $R^5$ is cyclopentadiene or pentamethyl cyclopentadiene, wherein said platinum group metal compound is provided in an amount effective to supply from 0.01 to 1.0 parts per million of platinum group metal per part of fuel and further wherein said platinum group metal compound is vaporized in the combustion chamber and travels to and replenishes the catalytic converter.

12. The method of claim 11 wherein $R^1$ and $R^3$ are phenyl or lower alkyl, $R^2$ is phenyl and $R^4$ is cyclopentadiene.

* * * * *

UNITED STATES PATENT AND TRADEMARK OFFICE
CERTIFICATE OF CORRECTION

PATENT NO. : 5,034,020
DATED : July 23, 1991
INVENTOR(S) : W. Robert Epperly and Barry Normand Sprague It is certified that error appears in the above—identified patent and that said Letters Patent is hereby corrected as shown below:

At col. 3, line 43, "$L^1M^2R^{57}$" should read --$L^1M^2R^5$--;

At col. 11, line 15, "cyclopetadiene" should read --cyclopentadiene--;

At col. 11, line 15, "pentamnethyl" should read --pentamethyl--;

At col. 11, line 20, "10.0" should read --1.0--;

At col. 11, line 39, "form" should read --from--; and

At col. 12, line 23, "coclopentadiene" should read --cyclopentadiene--.

Signed and Sealed this

Fifteenth Day of December, 1992

Attest:

DOUGLAS B. COMER

Attesting Officer        Acting Commissioner of Patents and Trademarks